United States Patent [19]

Buchner

[11] 4,174,705
[45] Nov. 20, 1979

[54] ULTRASONIC IMAGING APPARATUS OPERATING ACCORDING TO THE IMPULSE-ECHO METHOD

[75] Inventor: Klaus Buchner, Uttenreuth, Fed. Rep. of Germany

[73] Assignee: Siemens Aktiengesellschaft, Berlin & Munich, Fed. Rep. of Germany

[21] Appl. No.: 804,498

[22] Filed: Jun. 8, 1977

[30] Foreign Application Priority Data

Jun. 25, 1976 [DE] Fed. Rep. of Germany ....... 2628568

[51] Int. Cl.² .................. G01S 9/66; A61R 10/00
[52] U.S. Cl. .......................... 128/660; 73/626; 358/112; 73/609; 367/7
[58] Field of Search .......... 128/2 V, 2.05 Z; 73/618-626; 358/112, 609-614; 340/1 R, 5 MP

[56] References Cited

U.S. PATENT DOCUMENTS

| | | | |
|---|---|---|---|
| 3,651,253 | 3/1972 | Morgand et al. | 340/5 MP |
| 3,778,757 | 12/1973 | Houston | 340/5 MP |
| 3,792,194 | 2/1974 | Wood et al. | 358/112 X |
| 3,864,660 | 2/1975 | Ranalli et al. | 128/2 V X |
| 3,919,683 | 11/1975 | Itamura et al. | 340/1 R |
| 3,954,098 | 5/1976 | Dick et al. | 128/2 V X |
| 4,010,466 | 3/1977 | Hofstein | 340/1 R X |
| 4,034,744 | 7/1977 | Goldberg | 128/2 V |

Primary Examiner—Dalton L. Truluck
Assistant Examiner—Francis J. Jaworski
Attorney, Agent, or Firm—Hill, Van Santen, Steadman, Chiara & Simpson

[57] ABSTRACT

In the illustrated embodiment, an electronic receiving gate is inserted between the image display device and the ultrasonic echo receiver so as to allow only echo impulses from a selected depth of field to pass through to the image display device. The depth selection is effected without any change in the line and image scanning rates by shifting the receiving gate between its transmitting and blocking states in the rhythm of the line sweep pulses and by adjusting the moment of emission of the ultrasonic pulses within the blocking phase of the receiving gate.

6 Claims, 2 Drawing Figures

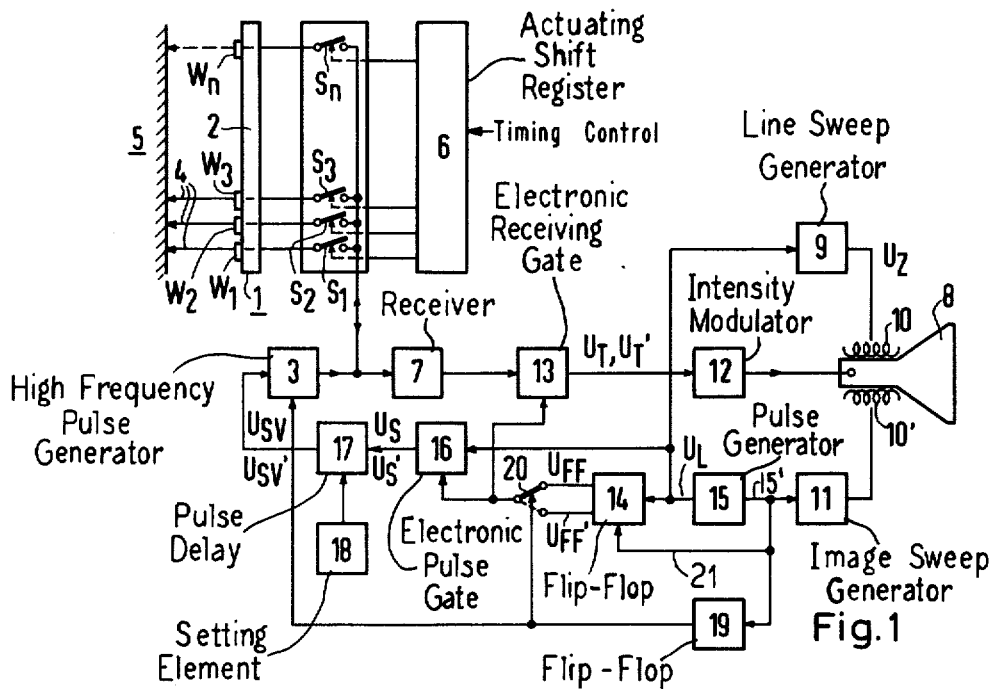
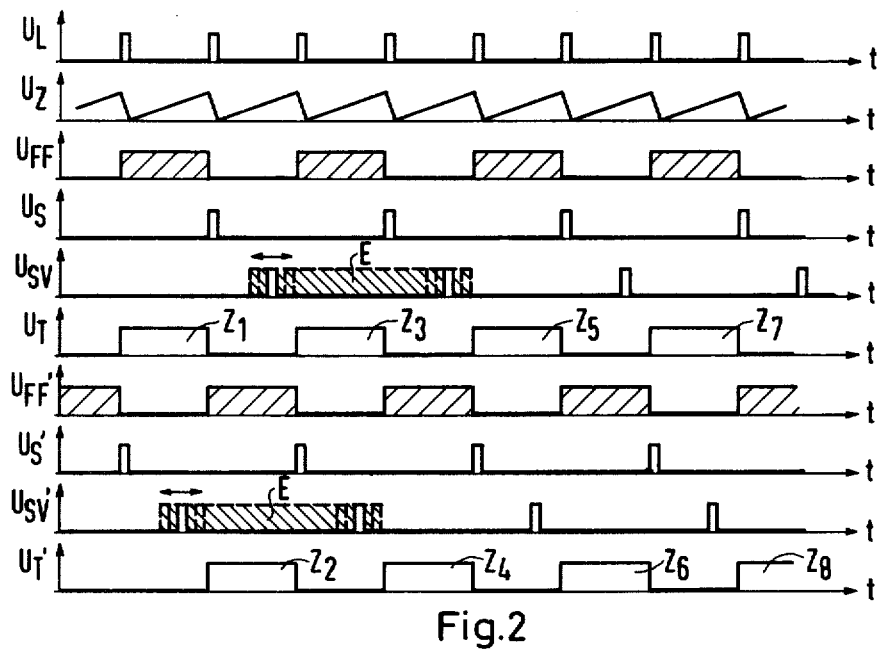
Fig.1
Fig.2

ULTRASONIC IMAGING APPARATUS OPERATING ACCORDING TO THE IMPULSE-ECHO METHOD

BACKGROUND OF THE INVENTION

The invention relates to an ultrasonic imaging apparatus operating according to the impulse-echo method, particularly for medical diagnostics, with an ultrasonic applicator for linear ultrasonic scanning of an examination subject and an image display device with a line generator for reproducing the echo pulses as lines and also an image generator for displacement of lines as a function of the displacement of the ultrasonic beam in the subject, there being inserted between the image display device and the ultrasonic applicator a controllable electronic receiving gate which allows only echo pulses from an adjustable depth of field of the examination subject to pass through to the image display device.

Ultrasonic imaging apparatus with electronic receiving gates for limiting the zone of representation of echo signals are previously known, for example, from the German Offenlegungsschrift Nos. 1,928,366 and 2,060,260. In these video apparatus, however, in the case of an ultrasonic scanning process line-by-line in parallel superposed planes, the problem consists of obtaining echo impulses only from those planes or curved surfaces of the examination subject which lie substantially vertical to the direction of irradiation of the ultrasound into the examination subject, i.e. vertical to the scanned planes. For this purpose, the receiving gate has to be adjusted to relatively narrow receiving, such adjustment of the gate corresponding to the transmission of echo signals produced by a given ultrasonic pulse within a relatively narrow time interval corresponding to a relatively narrow depth range where depth is taken in the direction of propagation of the ultrasonic energy. However, independently thereof, the problem which also frequently arises in ultrasonic sectional image diagnostics consists in that a limitation of range must be effected within the plane scanned by the ultrasonic beam, such that echo impulses from only a limited depth range in the scanning plane are received and represented on the display device. It is thus possible to block out those parts of the ultrasonic sectional image which are not of interest from the image representation so that only the parts actually of interest are presented to the viewer.

SUMMARY OF THE INVENTION

It is the object of the present invention to construct an ultrasonic imaging apparatus of the type specified at the outset such that such a restriction of field at any desired depths of the examination subject is ensured with the simplest technical means, whereby a depth selection is to be effected without any change in the line- and image-frequency.

According to the invention, the task is solved in that the electronic receiving gate is operated alternately in the opened and closed state in the rhythm of sweep pulses of the line sweep generator, whose sweep frequency amounts to a multiple of the sequence frequency (or repetition rate) of the transmitting/receiving cycle of the ultrasonic applicator, and in that only within those phases wherein the receiving gate is closed for echo pulses is a transmitting pulse produced for the ultrasonic applicator, the moment of emission of the transmitting pulse being capable of random displacement (or shifting) within the closed phase of the receiving gate.

In the apparatus in accordance with the invention, the displacement of a selection zone for echo impulses is effected solely by way of alteration of the moment of emission of the transmitting pulse within the closed phase of the receiving gate. Since otherwise the opening times of the receiving gate are in fixed synchronism with the line sweeps of the line sweep voltage of the line sweep generator, opening times of the receiving gate always result in regularly recurring fixed periods, these, however, effecting a displacement of the zone of representation since, with a changed moment of emission of the transmitting pulse, the zone of representation is correspondingly relatively changed.

Other objects, features and advantages of the invention will be apparent from the following detailed description taken in connection with the accompanying sheet of drawings.

BRIEF DESCRIPTION OF THE DRAWINGS

FIG. 1 is a basic electric circuit diagram showing an ultrasonic imaging apparatus in accordance with the invention; and FIG. 2 shows a pulse diagram for explaining the operation of the embodiment of FIG. 1 during operation of the ultrasonic applicator in an interlaced scanning mode.

DETAILED DESCRIPTION

In FIG. 1 is designated by 1 the ultrasonic applicator which in the present case is constructed as an ultrasonic array. The applicator 1 accordingly comprises a plurality of ultrasonic transducers $W_1$ to $W_n$ (piezoelectric crystal plates) which are supported adjacently in a row on a carrier part 2 consisting of material which effectively attenuates ultrasonic waves. The individual transducer elements $W_1$ to $W_n$ can be selectively excited either individually or in groups by way of high frequency pulses of a high frequency pulse generator 3 so that they radiate ultrasonic pulses into an examination subject 5, e.g. a human body, in the direction of the arrows 4. Actuating individual transducer elements $W_1$ to $W_n$ in individual or group formation is effected by means of an actuating device which comprises, in the normal manner, actuating shift register 6 under timing control and actuating switches $S_1$ to $S_n$ for connecting the transducer elements to be excited (or energized) to the high frequency pulse generator 3 in transmitting operation or to an echo pulse receiving amplifier 7 in receiving operation. The actuating device in this instance acts with the shift register 6 such that the individual transducer elements $W_1$ or $W_n$, respectively, can be switched in continuous succession individually or in groups to transmit or receive, by way of correspondingly actuated switches $S_1$ to $S_n$. There thus results a linear progression of the ultrasonic transmitting/receiving beam across the row of transducers and thus, correspondingly, linear ultrasonic scanning of the examination subject 5. In the exemplified embodiment according to FIG. 1, the ultrasonic scanning is effected in the interlaced method. For this reason, the transducer elements $W_1$ to $W_n$ of the array 1 can be controlled by way of shift register 6 and control switches $S_1$ to $S_n$ that, during a respectively first scanning process, the examination subject 5 is always scanned, e.g. only in odd-numbered ultrasonic lines in each case, and only in the successive second passage is it scanned in the intermediate even-numbered ultrasonic lines. In this way there result two successive ultrasonic half images which accordingly must be summated to form the full image on an image recording device. In the exemplary embodiment according to FIG. 1, there serves as image recording device specifically an electron beam tube 8 to which there is coordinated in a conventional manner a line sweep generator 9 for a horizontal deflection coil 10 and an image sweep generator 11 for the vertical deflection coil 10' of the electron beam tube 8. The electron beam tube 8 further also comprises an intensity modulator 12 for intensity modulation of the image lines in the rhythm of the echo pulses occurring.

To restrict the echo receiving range (or zone) in the depth direction to a desired area of representation there serves an electronic gate 13 and intensity modulator 12 of the electron beam tube 8. The control of the gate 13 for alternate opening and closing is effected as a function of output signals $U_{FF}$ or $U_{FF}'$ of a bistable flip-flop 14 which in turn is switched over by way of control clock pulses $U_L$ of a control clock pulse generator 15. The control clock pulse generator 15 serves simultaneously for control of the line sweep generator 9 to produce line sweep pulses $U_Z$ in the rhythm of the control clock pulses of the control clock pulse generator 15 over successive complete image cycles. The control clock pulse generator 15 further controls with its control clock pulses, by way of a further electronic pulse gate 16 and a pulse delay member 17 (e.g. a monostable flip-flop), the high frequency pulse generator 3. The delay 17 produces a trigger pulse $U_{SV}$ or $U_{SV}'$ each such pulse serving to trigger a high frequency pulse from generator 3 for the transducers of the ultrasonic array. The opening of the gate 16 is effected in turn with the output pulses of the bistable flip-flop 14, but in alternate operation (or "alternate mode") relative to the gate 13. To the pulse delay member 17 there is further coordinated a setting (or adjusting) element 18 for setting various delay times. For the automatic switch-over from ultrasonic scanning in the first half image to ultrasonic scanning in the second half-image and vice versa, there serves a further bistable flip-flop 19 in conjunction with a change-over switch 20 between the two outputs of the bistable flip-flop 14. The bistable flip-flop 19 is switched over in the rhythm of the image sweep pulses for the image sweep generator 11 which are obtained from the control clock pulses of the control clock pulse generator 15 through suitable scaling for example by means of a pulse rate divider within component 15 having an output 15' for supplying half-image rate pulses to components 11, 14 and 19. Simultaneously with this switch-over of the bistable flip-flop 19 at the end of an image sweep, the bistable flip-flop 14 is also reset to the starting condition via the reset line 21.

The method of operation of the basic circuit diagram according to FIG. 1 will be apparent in conjunction with the pulse diagram according to FIG. 2 as follows:

The control clock pulse generator 15 always produces at its clock pulse output a series of pulses $U_L$ (herein termed control clock pulses) independently of the respective half-image construction (or formation). Correspondingly, the line sweep generator 9 also always produces a line sweep voltage $U_Z$ in the pattern according to FIG. 2. The actuation of the two gates 13, 16 by the output pulses of the bistable flip-flop 14, however, is fixed differently for each half-image. For the first half-image, for example, the switch 20 is located in the illustrated switching position. The bistable flip-flop 14 thus supplies output pulses $U_{FF}$ according to FIG. 2 with half the clock pulse frequency of the control clock pulse $U_L$. In the rhythm of these pulses $U_{FF}$ the two gates 13, 16 are opened and closed again in push-pull (or counter rhythm) fashion such that in the hatched area of the pulse series $U_{FF}$ only the gate 13 is opened in each case and in the following zero phase the gate 16 is opened in each case. Due to this switch-over mechanism at the two gates 13, 16, only those clock pulses of the control clock pulse generator 15 pass through the gate 16 to the delay member 17 and, after a suitable delay, also to the transmitting pulse generator 3, which coincide with the respective opening time of the gate 16. These through-pulses are designated in FIGS. 1 and 2 by $U_S$ and the corresponding delayed pulses by $U_{SV}$. Each pulse $U_{SV}$ reaching the high frequency pulse generator 3 effects by way of the latter the radiation of an ultrasonic transmitting pulse into the examination subject. The echo pulses received as a result of this are passed via the echo receiving amplifier 7 to the gate 13. Since this gate 13 is opened in alternate rhythm relative to the gate 16, however, passage for echo pulses is produced only in a limited area of the entire receiving zone E, FIG. 2, between two transmitting pulses $U_{SV}$, which is prescribed by the respectively hatched areas of the voltage $U_{FF}$ of the bistable flip-flop 14. Since the scanning of the first half-image is effected in odd-numbered scanning lines in each case, limited echo pulse sequences occurring during intervals $Z_1$, $Z_3$, $Z_5$, etc. of $U_T$ are thus produced at the output of the gate 13, these being supplied via the intensity modulator 12 of the tube 8 for intensity modulation of the image line being produced at this particular moment by the line sweep generator 9. From the pattern of transmitted line information $Z_1$, $Z_3$, $Z_5$, $Z_7$, etc., of the gate voltage curve $U_T$ it can now be clearly seen that, irrespective of the moment of occurrence of the delayed transmitting-trigger pulse $U_{SV}$, the position of the pulses $Z_1$, $Z_3$, $Z_5$, etc., is always determined only by the opening times of the pulses $U_{FF}$ of the bistable flip-flop 14 for the gate 13. It is thus possible, in a simple manner, to correspondingly restrict the zone of representation of echo pulses to any random subject depths, through corresponding shifting of the pulses $U_{SV}$ (indicated in broken lines in FIG. 2), which, according to FIG. 1, is effected by setting (or adjusting) various delay times by means of the setting (or adjustment) element 18 on the delay member 17. This shift is effected, however, with constant line and image frequency, only as a result of change in the moment of radiation of ultrasonic transmitting pulses by means of the delay member 17. The line construction (or formation) for the even-numbered lines of the second half-image is effected in a similar manner as in the first half-image. These lines, however, need only be shifted relative to the odd-numbered lines by a corresponding time interval. This is effected automatically by means of the switch 20, which, in each case, at the end of an ultrasonic scanning of a first half-image, is moved into the switching position, indicated by broken lines, by way of the bistable flip-flop 19 which is switched over at this moment. Thus, at the output of the bistable flip-flop 14, the inverse voltage $U_{FF}'$ is obtained, which, delayed respectively by half the transmitting/receiving time, produces a switchover of gates 13 or 16, respectively, in counter rhythm as well as producing transmitting-trigger-signals $U_{S'}$ and $U_{SV'}$. Area-restricted line pulses $Z_2$, $Z_4$, $Z_6$, $Z_8$ are thus produced at the output of gate 13 which are correspondingly inserted as the missing even-numbered lines into the spaces between the odd-numbered lines of the first half image on the display 8.

For operating ultrasonic applicator 1 in the interlaced scanning mode, the shift register 6 may comprise two series of shift register stages, one series being in control of the odd-numbered switches $S_1$, $S_3$..., while the other series of shift register stages would be in control of the even-numbered switches such as $S_2$. Prior to the beginning of the scanning interval $Z_1$ of waveform $U_T$, FIG. 2, a pulse such as an initial $U_S$ pulse (not shown) would set the first stage of the first series of shift register stages to close switch $S_1$. At the end of the first line display interval $Z_1$, FIG. 2, a pulse corresponding to the first illustrated pulse $U_S$ would actuate the first series of shift register stages so as to set the second stage, opening the switch $S_1$ and closing the switch $S_3$. Thus, each of the pulses $U_S$ would initiate closure of a different odd-numbered switch during a first of the interlaced scanning cycles. At the completion of the scanning of the odd-numbered transducer elements, the first pulse $U_S'$ could clear all of the register stages of the first series, and serve to set the first stage of the second series, resulting in the closure of switch $S_2$. Then the successive pulses $U_S'$ would result in the successive closure of the even-numbered switches and the corresponding activation of the even-numbered transducer elements in sequence during the second interlaced scanning cycle. Group operation of applicator 1 might involve loading binary ones into the first four stages of an n-stage shift register to initiate the first odd-line scan, and doubling shifting the four binary ones by two places for each $U_S$ pulse. Even line scanning would be initiated by loading the four binary ones into the second through fifth stages of the shift register.

It will be apparent that many modifications and variations may be effected without departing from the scope of the novel concepts and teachings of the present invention.

I claim as my invention:

1. Ultrasonic imaging apparatus operating according to the impulse-echo method, particularly for medical diagnostics, with an ultrasonic applicator for linear ultrasonic scanning of an examination subject and an image display device with a line sweep generator for reproducing echo impulses as lines, as well as an image generator for displacement of the lines as a function of the displacement of the ultrasonic beam in the subject, and a controllable electronic receiving gate having an output connected to said image display device for controlling the time interval in which echo impulses produced by the ultrasonic beam are displayed during each line sweep operation of the line sweep generator, wherein the improvement comprises means operatively coupled with said electronic receiving gate for operating said receiving gate alternately in the opened and blocking state in synchronism with the sweep pulses of the line sweep generator, control means operatively synchronized with the opened and blocking states of the electronic receiving gate for controlling the repetition rate of the transmitting cycles of the ultrasonic applicator and providing for establishing an independent operating frequency for the line sweep generator equal to a multiple of said repetition rate, and common timing means operatively coupled with said control means and providing for common adjustment of the timing of a series of transmitting pulses and providing for the generation of said transmitting pulses only within respective blocking phases wherein the receiving gate is in the blocking state for echo impulses, said common timing means being adjustable for common adjustment of the moment of emission of each transmitting pulse within a respective blocking phase of the receiving gate thereby to provide a common adjustment of the depth location along the respective scanning paths being displayed on the image display device without alteration of the timing of the line sweep generator.

2. Ultrasonic imaging apparatus according to claim 1, characterized in said control means comprising a clock pulse generator operatively synchronized with the opened and blocking states of the electronic receiving gate and providing for establishing an independent operating frequency for the line sweep generator equal to a multiple of said repetition rate and supplying control clock pulses ($U_L$) controlling the operating frequency of the line sweep generator for producing line sweep pulses ($U_Z$) in synchronism with said control clock pulses, said control means further comprising a further pulse gate operatively connected to said control clock pulse generator for transmitting pulses ($U_S$) for controlling the repetition rate of the transmitting cycles of the ultrasonic applicator and synchronized with control clock pulses occurring only during the blocking phases of the receiving gate, and said common timing means being operatively coupled with said further pulse gate for common adjustment of the timing of a series of transmitting pulses ($U_{SV}$), said common timing means being adjustable for common adjustment of the moment of emission of each transmitting pulse relative to the occurrence of a corresponding control clock pulse, so as to provide a common adjustment of the occurrence of successive transmitting pulses within respective blocking phases of the receiving gate.

3. Ultrasonic imaging apparatus according to claim 2, characterized in said means operatively coupled with said electronic receiving gate for operating said receiving gate comprising a bistable flip-flop coupled with said gates for switching the gates between the opened and the blocking states with opposite phase, said flip-flop being operatively coupled with said control clock pulse generator for actuation in synchronism with said control clock pulses.

4. Ultrasonic imaging apparatus according to claim 3, characterized in said means operatively coupled with said electronic receiving gate further comprising a change-over switch for switching over the phase of operation of the electronic receiving gate and the further pulse gate in response to image sweep pulses coordinated with ultrasonic half-images produced in an interlaced scanning process.

5. Ultrasonic imaging apparatus according to claim 4, characterized in said means operatively coupled with said electronic receiving gate further comprising a second bistable flip-flop which is operated in synchronism with the image sweep pulses and having its output controlling said change-over switch so that the switch-over of the change-over switch is effected in synchronism with the image sweep pulses.

6. Ultrasonic imaging apparatus according to claim 1, characterized in said common timing means comprising a delay member and a setting device for setting said delay member to various delay times, said setting device in conjunction with said delay member providing for common adjustment of the moment of emission of each transmitting pulse within a respective blocking phase of the receiving gate thereby to provide a common adjustment of the depth location along the respective scanning paths being displayed on the image display device without alteration of the timing of the line sweep generator.

* * * * *